United States Patent [19]

Szoka, Jr. et al.

[11] 4,394,448
[45] Jul. 19, 1983

[54] METHOD OF INSERTING DNA INTO LIVING CELLS

[76] Inventors: Francis C. Szoka, Jr., 76 Summit St., Waltham, Mass. 02154; Demetrios P. Papahadjopoulos, 3170 Condit St., Lafayette, Calif. 94549

[21] Appl. No.: 143,455

[22] Filed: Apr. 24, 1980

Related U.S. Application Data

[63] Continuation-in-part of Ser. No. 881,116, Feb. 24, 1978, Pat. No. 4,235,871.

[51] Int. Cl.³ .......................................... C12N 15/00
[52] U.S. Cl. ...................... 435/172; 424/19; 435/317; 435/820
[58] Field of Search ............... 435/172, 317; 424/19

[56] References Cited

U.S. PATENT DOCUMENTS

| 4,186,183 | 1/1980 | Steck | 424/19 X |
| 4,217,344 | 8/1980 | Vanlerberghe | 424/19 X |
| 4,235,871 | 11/1980 | Papahadjopoulos | 424/19 |
| 4,241,046 | 12/1980 | Papahadjopoulos | 424/19 |

OTHER PUBLICATIONS

R. T. Fraley et al., Proc. Natl. Acad. Sci. USA, 76 (7), 3348-3352 (Jul. 1979).
G. Gregoriadis, The New England Journal of Medicine, 295 (14), 765-769 (1976).
Chemical Abstracts, 82:119546r (1975).
Chemical Abstracts, 84:1325f (1976).
Chemical Abstracts, 85:137237g (1976).
Chemical Abstracts, 91:71257d (1979).

*Primary Examiner*—Sidney Marantz
*Attorney, Agent, or Firm*—Kane, Dalsimer, Kane, Sullivan & Kurucz

[57] ABSTRACT

A method of inserting deoxyribonucleic acid or fragments thereof into a living cell, which comprises; encapsulating the DNA or fragment in a lipid vesicle and bringing the vesicle in contact with said cell, whereby insertion occurs.

11 Claims, No Drawings

METHOD OF INSERTING DNA INTO LIVING CELLS

CROSS-REFERENCE TO RELATED APPLICATION

This application is a continuation-in-part of our copending U.S. patent application Ser. No. 881,116 filed on Feb. 24, 1978 and now issued as U.S. Pat. No. 4,235,871.

BACKGROUND OF THE INVENTION

1. Field of the Invention

The invention relates to methods of inserting deoxyribonucleic acids and fragments of deoxyribonucleic acids into living cells, including mammalian cells.

2. Description of the Prior Art

Prior to our invention, lipid vesicle encapsulation techniques have not been available for the efficient encapsulation of large macromolecules such as deoxyribonucleic acid. The deoxyribonucleic acid molecule is relatively large; i.e.; on the order of about 20 angstroms in thickness and having lengths of circa 30,000 angstroms. By the method of our invention, more fully described in our copending patent application Ser. No. 881,116 filed Feb. 24, 1978, and issued as U.S. Pat. No. 4,235,871, these large macromolecules are efficiently encapsulated in oligolamellar lipid vesicles.

In addition, the structure of the prior art lipid vesicles has not been conducive to utilization of the encapsulated deoxyribonucleic acids. Cellular uptake of multilamellar vesicles and/or their contents appears to be less efficient than has been experienced with monolamellar or oligolamellar structured lipid vesicles.

SUMMARY OF THE INVENTION

The invention comprises a method of inserting deoxyribonucleic acid (DNA) or fragments thereof into a living cell, which comprises; encapsulating the acid or fragment in a lipid vesicle and bringing the vesicle in contact with said cell, whereby insertion occurs. By the method of the invention, encapsulated DNA or fragments thereof can be inserted into living cells, both plant and animal through the delivery vehicle of the lipid vesicle. The advantage is in labor and time saving over present methods which comprise the well known plasmid and splicing techniques. Also, the vesicle encapsulated DNA is protected from degradation by certain enzymes, providing further advantages in the method of the invention.

The term "living cell" as used herein means a cell of a living organism, plant or animal, unicellular such as a microorganism like *E. coli* and like microorganisms or multicellular including mammals such as humans and the like.

DETAILED DESCRIPTION OF THE PREFERRED EMBODIMENTS OF THE INVENTION

Deoxyribonucleic acid (hereinafter referred to at times as "DNA" for convenience) or fragments thereof may be encapsulated within a lipid vesicle by the method of our pending patent application, Ser. No. 881,116 filed on Feb. 24, 1978 and issued as U.S. Pat. No. 4,235,871. The method comprises:

(1) providing a mixture of a vesicle wall forming compound in organic solvent and an aqueous mixture of the DNA material to be encapsulated, the ratio of organic phase to aqueous phase being that which will produce an emulsion of the water-in-oil type;

(2) forming a homogeneous emulsion of said mixture, of the character produced by ultra-sonic radiation;

(3) evaporating organic solvent from the emulsion, whereby a mixture is obtained having a gel-like character; and (4) converting the gel-like mixture to synthetic, oligolamellar vesicles encapsulating the DNA material.

The term "synthetic, oligolmellar lipid vesicles (liposomes)" as used herein means man-made lipid vesicles, created in the laboratory and characterized in part by few or single bimolecular lipid layers forming the vesicle walls.

The first step in the preparation of encapsulated DNA is to provide a mixture of a lipid vesicle wall forming composition in organic solvent and an aqueous mixture of the DNA material to be encapsulated in the vesicle. Vesicle wall forming compounds are generally well known as are the methods of their preparation. For example, any number of phospholipids or lipid compounds may be used to form the vesicle walls. Representative of such wall forming compounds are; phosphatidylcholine (hereinafter referred to as "PC"), both naturally occurring and synthetically prepared, phosphatidic acid (hereinafter referred to as "PA"), lysophosphatidylcholine, phosphatidylserine (hereinafter referred to as "PS"), phosphatidylethanolamine (hereinafter referred to as "PE"), sphingolipids, phosphatidylglycerol (hereinafter referred to as "PG"), spingomyelin, cardiolipin, glycolipids, gangliosides, cerebrosides and the like used either singularly or intermixed such as in soybean phospholipids (Asolectin, Associated Concentrates). In addition, other lipids such as steroids, cholesterol, aliphatic amines such as long chain aliphatic amines and carboxylic acids, long chain sulfates and phosphates, dicetyl phosphate, butylated hydroxytoluene, tocophenol, retinol, and isoprenoid compounds may be intermixed with the phospholipid components to confer certain desired and known properties on the formed vesicles. In addition, synthetic phospholipids containing either altered aliphatic portions such as hydroxyl groups, branched carbon chains, cycloderivatives, aromatic derivatives, ethers, amides, polyunsaturated derivatives, halogenated derivatives or altered hydrophillic portions containing carbohydrate, glycol, phosphate, phosphonate, quaternary amine, sulfate, sulfonate, carboxy, amine, sulfhydryl, imidazole groups and combinations of such groups can be either substituted or intermixed with the above mentioned phospholipids and used in the process of the invention. It will be appreciated from the above that the chemical composition of the lipid component of the vesicles prepared by the method of the invention may be varied greatly without appreciable diminution of percentage capture although the size of the vesicle may be affected by the lipid composition. A convenient mixture we have used extensively and which is representative of lipid mixtures advantageously used in the method of the invention is composed of PS and PC, or PG and PC as identified above (advantageously at a 1:4 molar ratio in each instance). The PC, PG, PA and PE, may be derived from purified egg yolk. Saturated synthetic PC and PG, such as dipalmitoyl may also be used. Other amphipathic lipids that may be used, advantageously also at 1:4 molar ratios with PC, are gangliosides, globosides, fatty acids, stearylamine, long chain alcohols, and the like.

The liposome wall forming composition may be initially provided dissolved in any inert solvent that can be substantially removed from the lipid or phospholipid compound when desired. Representative of such solvents are a wide variety of eithers, esters, alcohols, ketones, hydrocarbons (aromatic and aliphatic including fluorocarbons), and silicones in which an aqueous phase does not have an appreciable solubility. The solvents may be used either alone or in admixture. For each solvent or mixture of solvents however, the optimal ratio of lipid, aqueous space, and solvent is different and must be determined for each case by trial and error techniques as will be appreciated by those skilled in the art. The term "inert solvent" as used herein means a solvent for the lipid or phospholipid, which will not interfere with or otherwise adversely affect the desired course of the method of the invention.

The phospholipid or lipid along with any lipid-soluble additives, are advantageously evaporated from their solvent on to the sides of a suitable reaction vessel. The organic phase, in which the "reverse phase evaporation vesicles" of the invention will be formed is then added to the vessel, i.e., an inert organic solvent for the lipids and phospholipids as described above. With mixing, dissolution of the lipid component of the vesicles to be formed, previously deposited on the vessel walls is obtained. A number of inert organic solvents are preferred for forming the organic phase according to the method of the invention, depending on the following conditions of the method employed. For low temperature conditions, i.e., removal subsequently of the organic phase at relatively low temperatures, we find diethyl ether most advantageous, although chloroform, or tetrahydrofuran may also be used advantageously. For higher temperature processing, isopropyl ether is a preferred inert organic solvent, particularly for preparing lipid vesicles containing saturated phospholipids as the lipid component. Following dissolution of the phospholipid or lipid to form the organic phase, an aqueous phase is added to obtain a heterogeneous 2-phase mixture. The aqueous phase contains in dissolution/suspension the DNA materials to be encapsulated in the synthetic lipid vesicles. Preferably the aqueous phase is buffered to a pH suitable to maintain stability of the DNA material for encapsulation. The ionic strength of the aqueous phase has a bearing on the encapsulation efficiency obtained in the method of the invention. As a general rule, the higher the ionic strength of the aqueous phase, the lower the percentage of entrapment. For example, with 15 mM sodium chloride present, one can encapsulate circa 60 percent of the aqueous phase, while with 500 mM sodium chloride present, only about 20 percent of the aqueous phase may be encapsulated. Thus, to maximize the encapsulation of macromolecules, a buffer of low ionic strength (less than 0.3) is preferably employed. The encapsulation efficiency is also dependent to some degree on the concentration of lipid or phospholipid present in the 2-phase system. Preferably the proportion of lipid or phospholipid component is within the range of from about 0.5 mg to about 50 mg/ml. of the inert organic solvent. Preferably the ratio of organic phase to aqueous phase is within the range of from about 2:1 to about 20:1 v/v, most preferably about 4:1 to form a water-in-oil emulsion.

The heterogeneous 2-phase mixture obtained as described above is then emulsified to obtain an emulsion of the character produced by ultrasonic radiation. Preferably this is accomplished with the use of a bath type sonicator, or for large volume preparations in an industrial size emulsifier. Generally, the 2-phase mixture is sonicated for about 3 to 5 minutes, or until either a clear 1-phase mixture or a homogeneous emulsion forms. This is achieved by simply placing the container vessel in the sonicating bath at an optimal level. Emulsification may be carried out over a wide range of temperatures, i.e., from about 10° to about 50° C., advantageously at a temperature of from 0°-20° C. The optimum conditions under which emulsification is carried out depends upon the solvent, phospholipid, and volume of aqueous phase used in the preparation. It will be appreciated that trial and error techniques may be used to determine the optimum conditions for emulsification. The emulsion mixture is then treated to remove a substantial portion of the inert organic solvent. This may be carried out conveniently by use of a rotary evaporator, at a temperature of circa 20° C. to 60° C. and under a reduced pressure, i.e.; under vacuum (10 mm to 50 mm Hg). The temperature employed for evaporation of the organic solvent from the emulsion depends on the boiling point of the particular organic solvent used in the emulsion and the stability of the DNA material being encapsulated. During evaporation, the emulsion first becomes a viscous gel, which is an intermediate product. The gel is stable and can be stored in this state for short periods of time, up to a week (at least), at 4° C. under an inert atmosphere such as nitrogen gas. A small amount of water or buffer can then be added to the gel and the resulting mixture evaporated for an additional period (circa 15 minutes) to help remove residual traces of the gel into a homogeneous-appearing, suspension to oligolamellar lipid vesicles. The gel may be converted by agitation or by dispersion in a aqueous media such as a buffer solution. The vesicles obtained range in diameter from 2,000 to 4,000 Angstroms (average). A significant proportion of the DNA materials for encapsulation contained in the aqueous buffer is captured within the lipid vesicles (up to circa 60 percent, depending on the amount of lipid, volume of the aqueous phase, ratio of the organic phase to aqueous phase to lipid, type of inert organic solvent(s) and, type of lipid(s) used in the process). The non-incorporated aqueous material may be removed of necessary by appropriate and known techniques such as by repeated centrifugations, column chromatography, ion exchange chromatography, dialysis and like procedures. The lipid vesicles with their encapsulated DNA contents can then be suspended in any isotonic buffer for use. The vesicles may be sterilized by passage through a 0.4 micron filter (nucleopore) when sterility is desired.

Advantageously the method of preparing the DNA containing vesicle is carried out under an inert atmosphere. The term "inert atmosphere" as used herein means a non-oxidizing atmosphere such as an atmosphere of nitrogen gas, argon and like inert gases.

The encapsulated DNA material is inserted into the living cell by contact of the encapsulating lipid vesicle with the cell plasma membrane. In the case of cells associated with multi-cellular organisms, contact may be in-vivo or in-vitro. The encapsulated DNA materials are passed into the cell (inserted) when the encapsulating lipid vesicle contacts the cell and is taken up by the living cell through fusion of the lipid vesicle with the cellular plasma membrane or by endocytosis. There is evidence that vesicle uptake may be by both mechanisms. In any event the DNA material is taken up by the living cell and the encapsulated DNA material incorporated within the living cell.

Generally, the rate of uptake by the living cell is influenced by a number of factors including ambient temperature, lipid concentration and the charge on the lipid vesicle surface. A positive charge on the surface of the lipid vesicle enhances uptake. The rate of uptake is directly proportional to the ambient temperature and increases with temperature. Generally, cellular uptake is satisfactory within a temperature range of from about 0° to 40° C. Optimum temperature may be determined by trial and error techniques. Of course, selection of a given temperature will also depend upon whether the insertion of DNA material is being made in-vivo or in-vitro to living cells.

Techniques of bringing the lipid vesicles into contact with the living cells are conventional and include previously known techniques. For example if the contact is to be effected in-vitro, a simple admixture of cells and lipid vesicles is brought about. In-vivo, the lipid vesicles may be injected intravenously into the host organism, in a pharmaceutically acceptable carrier such as a saline suspension of appropriate pH.

The following examples describe the manner and process of making and using the invention and represent the best mode contemplated by the inventors, but are not to be construed as limiting.

EXAMPLE 1

Encapsulation of Mammalian Chromosomes in Phospholipid Vesicles

Chinese hamster chromosomes are prepared by the method of Matsui et al J. Cell Biol. 75, 121a, (1977) in a solution containing 10 mM tris(hydroxymethyl)aminomethane hydrochloride (pH 7.5), 2.5 m $MgCL_2$, 2.0 mM $CaCl_2$, and 0.5 mM phenylmethylsulfonyl fluoride (buffer T).

A suspension of the chromosomes in 60 μl. of buffer T is added to 1 ml. diethylether containing 2μ moles of total lipid composed of phosphatidylglycerol/phosphatidylcholine/cholesterol/N-4-nitro-benz-2-oxa-1,3-diazole phosphatidylethanolamine (NBD-PE; mole ratios 10/40/50/5) and sonicated in a bath-type sonicator under nitrogen for 3 minutes at 0°–5° C. The diethyl ether is removed on a rotary evaporator under reduced pressure and the resulting suspension is removed from the flask with 1.0 ml buffer T. The chromosomes are stained with 5 μl of an ethidium bromide solution and the vesicle-chromosome suspension is examined under a fluorescent microscope (excitation 460 nm, emission 520 nm). The bilayer of the vesicles appears intense yellow due to the inclusion of the fluorescent phospholipid NBD-PE. The chromosomes appear as intense red structures. The color difference between the two fluorescent probes conveniently allows one to determine whether or not a chromosome has a lipid bilayer surrounding it.

EXAMPLE 2

Transfer of an Encapsulated Chromosome

Chromosomes extracted from HELA cells by the technique of S. Matsui et al, supra., and encapsulated as detailed in Example 1 supra., are used to transform mouse cells A9 (obtained from Dr. T. Shows, Roswell Park Memorial Institute, Buffalo, New York) that are lacking the enzyme hypoxanthine quanine phosphoribosyltransferase (HGPRT). A vesicle suspension containing 100 nmoles of the encapsulated chromosomes is mixed with $1 \times 10^6$ A9 mouse cells in 1 ml Dulbecco's minimal essential medium without serum and incubated at 37° C. for 4 hours. At the end of this time the mouse cells are exposed to hypoxanthine/aminopterin/thymidine (HAT) medium and the clonal growth monitored. Assay shows the presence of HGPRT, indicating that encapsulated chromosomes are effective for transferring genetic information to a cell lacking the necessary information to form the HGPRT enzyme.

EXAMPLE 3

Encapsulation of a Plasmid and its Transfer to a Bacterium

The plasmid pBR 322 which carries tetracycline resistance is encapsulated in phosphatidyl glycerol vesicles as follows. 1 μg of pBR 322 in 0.1 ml of Dulbecco's phosphate buffered saline (PBS) is added to 0.3 ml diethyl ether containing 10μ moles of phosphatidylglycerol. The plasmid-containing lipid vesicles are prepared following the procedure in Example 1 supra. The vesicle preparation is then treated with 10 μl of a solution containing 5 μg/ml DNase to degrade unencapsulated DNA. The vesicles with encapsulated DNA are added to tetracycline sensitive E. coli RRI after they had been prepared by the method of Cohan et al., Proc. Natl. Acad. Sci., USA, 69, 2110, (1972). The transformed E. coli are selected on a tetracycline containing agar medium and observed to be resistant to tetracycline. The use of lipid vesicle encapsulated DNA leads to a substantial increase in the efficiency of plasmid transfer to the E. coli when compared to unencapsulated plasmid DNA uptake by the bacteria.

EXAMPLE 4

Encapsulation of Mouse DNA and its Transfer to Mouse Liver in vivo

Unfractionated mouse DNA isolated by the procedure of Maniatis et al., Cell 15, 681–701, (1978) from C57 BL/6J mice (black 6) is encapsulated in lipid vesicles composed of lactosyl cerebroside/phosphatidylserine/phosphatidylcholine/αtocopherol/cholesterol (mole ratio 1/1/4/0.1/4) as follows. 2 mg of black 6 DNA in 1 ml of buffer T is added to 3 ml of diethylether containing 30μ moles of the lipid. The encapsulation is carried out by the procedure described in Example 1, supra. Unencapsulated DNA is separated from the encapsulated DNA by centrifugation at $10,000 \times G$ for 10 minutes. The pellet containing the encapsulated DNA is resuspended and the separation procedure is then repeated two times. The encapsulated DNA is resuspended in PBS at a lipid concentration of 30μ moles per ml. Six female, 21–28 day old, balb/cBγJ (Balb-c) mice are injected in the tail vein with 0.2 ml of the liposome encapsulated DNA. The animals are placed in a metabolic cage with free access to water and animal chow and the total urine excreted in twenty-four hours is collected for 3 consecutive 24 hour periods. The successful transfer of a mouse gene is observed by analyzing the mouse urine for the appearance of mouse urinary protein 2 (mup 2). Balb-c mice lack the gene for synthesizing this protein, while Black 6 mice contain it (Szoka and Paigen, Genetics 90; 591–612, 1978). The appearance of this protein in urine from Balb-c mice which had received the liposome encapsulated DNA is quantitated by acrylamide electrophoresis following the method of Szoka and Paigen, Genetics 90; 597–612

(1978). The inclusion of lactosyl cerebroside in the lipid vesicle is advantageous to obtain high levels of gene transfer to the Balb-c mice. The technique of this example may also be used to transfer specific cloned DNA sequences to other species in vivo.

EXAMPLE 5

Encapsulation of a Large Plasmid and its Transfer to a Plant Cell Protoplast

The plant tumor plasmid Ti (Mol. weight $>100\times 10^6$) isolated from *Agrobacterium tumifaciens* is encapsulated in liposomes as follows: 33 μg DNA (Ti) in 0.33 ml of sorbitol buffer is added to 1.0 ml diethyl ether containing 10μ moles phosphatidylserine and 10μ moles cholesterol. The liposomes are prepared by the general procedure set forth in Example 1, supra. The non-encapsulated DNA is either degraded by DNase or separated on Ficoll density gradients by centrifugation. The amount of DNA encapsulated in liposomes is found to be 14.9 μg or 45% of the total amount added.

The liposomes containing the Ti plasmid are subsequently incubated with Nicotiana Tabacum (tobacco) protoplasts. The growth characteristics of the plant cells on hormone-free solid media indicate that liposome encapsulated Ti plasmid is at least 50-100 times more efficient than free Ti DNA in enhancing the ability of these cells to sustain non-self limiting growth on the hormone free media.

These results indicate that liposome-encapsulated DNA is extremely useful in plant cell genetics by enhancing the incorporation and expression of foreign DNA. The large enhancement could be explained by increased protection of the encapsulated DNA from degradative enzymes and/or enhanced delivery into the cellular interior. The method of encapsulation is found to be very efficient (45%) even for such large macromolecules as the Ti plasmid (M.W. $>100\times 10^6$).

The Ti plasmid is carried by virulent strains of *Agrobacterium tumifaciens* which is known to induce a neoplastic disease (Crown Gall) of dicotyledenous plants. During transformation, a portion of the Ti plasmid is transferred and incorporated in the recipient cells. Transformation confers the ability to synthesize the novel arginine derivatives nopaline and octopine to the recipient cells, as well as permitting non-self limiting growth on hormone-free solid media. Since the Ti plasmid is a natural vector which can promote the transfer, integration, and expression of foreign DNAs into plant cells, it is an extremely useful vehicle for introducing other genes into plant cells. Free Ti plasmid (without encapsulation into liposomes) can transform tobacco protoplasts only with a very low frequency ($1\times 10^{-5}$) probably due to enzymatic degradation. The method for Ti encapsulation in liposomes therefore provides a powerful and unique new tool for enhancing the cellular incorporation of such large DNA molecules.

What is claimed is:

1. A method of inserting deoxyribonucleic acid into a living cell, which comprises; encapsulating the acid material in a lipid vesicle and bringing the vesicle in contact with said cell, whereby insertion occurs.

2. A method of inserting deoxyribonucleic acid into a living cell, which comprises;
   providing the deoxyribonucleic acid material encapsulated in a lipid vesicle; and
   bringing the encapsulated material into contact with the cell, whereby insertion occurs.

3. A method of inserting deoxyribonucleic acid into a living cell, which comprises;
   (1) providing a mixture of a vesicle wall forming compound in organic solvent and an aqueous mixture of the deoxyribonucleic acid material to be encapsulated, the ratio of organic phase to aqueous phase being that which will produce a water-in-oil emulsion;
   (2) forming a homogeneous water-in-oil emulsion of said mixture, of the character produced by ultrasonic radiation;
   (3) removing organic solvent from the emulsion, whereby a mixture is obtained having a gel-like character;
   (4) converting the gel-like mixture to a suspension of synthetic, oligolamellar vesicles encapsulating the deoxyribonucleic acid material; and
   bringing the encapsulated material into contact with the cell, whereby insertion occurs.

4. The method of claim 1 wherein the living cell is an animal cell.

5. The method of claim 1 wherein the living cell is a unicellular microorganism.

6. The method of claim 5 wherein the microorganism is *E. coli*.

7. The method of claim 1 wherein the living cell is a plant cell.

8. The method of claim 1 wherein the living cell is a plant protoplast.

9. The method of claim 1 wherein the lipid vesicles are oligolamellar vesicles having an average diameter of 2,000 to 4,000 Angstroms.

10. A method of inserting a chromosome into a living cell, which comprises;
    providing the chromosome encapsulated in a lipid vesicle; and
    bringing the lipid vesicle into contact with the cell, whereby insertion occurs.

11. A method of inserting a plasmid into a living cell, which comprises;
    providing the plasmid encapsulated in a lipid vesicle; and
    bringing the lipid vesicle into contact with the cell, whereby insertion occurs.

* * * * *

UNITED STATES PATENT AND TRADEMARK OFFICE
CERTIFICATE OF CORRECTION

PATENT NO. : 4,394,448
DATED : July 19, 1983
INVENTOR(S) : Francis C. Szoka & Demetrios P. Papahadjopoulos It is certified that error appears in the above—identified patent and that said Letters Patent is hereby corrected as shown below:

At Col. 3, line 5; "eithers" should read -- ethers -- .

At Col. 4, line 32; "to" should read -- of -- .

At Col. 6, line 64; "591-612" should read -- 597-612 -- .

Signed and Sealed this

Twelfth Day of June 1984

[SEAL]

Attest:

Attesting Officer

GERALD J. MOSSINGHOFF

Commissioner of Patents and Trademarks